(12) United States Patent
Su et al.

(10) Patent No.: US 10,712,253 B2
(45) Date of Patent: Jul. 14, 2020

(54) SIMULATION DEVICE FOR INTERACTION BETWEEN DEEP RESERVOIR ROCK AND FLUID IN BASIN AND METHOD FOR USING SAME

(71) Applicant: Lanzhou Center for Oil & Gas Resources, Institution of Geology & Geophysics, CAS, Lanzhou, Gansu (CN)

(72) Inventors: Long Su, Gansu (CN); Yuhong Yuan, Gansu (CN); Haichang Yang, Gansu (CN); Shixin Zhou, Gansu (CN); Dongwei Zhang, Gansu (CN); Shengrong Tang, Gansu (CN); Jihui Lin, Gansu (CN)

(73) Assignee: Northwest Institute of Eco-Environment and Resources, Chinese Academy of Sciences, Lanzhou (CN)

( * ) Notice: Subject to any disclaimer, the term of this patent is extended or adjusted under 35 U.S.C. 154(b) by 94 days.

(21) Appl. No.: 16/163,557

(22) Filed: Oct. 17, 2018

(65) Prior Publication Data
US 2019/0187039 A1    Jun. 20, 2019

(30) Foreign Application Priority Data
Dec. 15, 2017   (CN) .......................... 2017 1 1347121

(51) Int. Cl.
*G01N 15/08*   (2006.01)
*G01N 33/24*   (2006.01)

(52) U.S. Cl.
CPC ....... *G01N 15/082* (2013.01); *G01N 15/0806* (2013.01); *G01N 33/24* (2013.01)

(58) Field of Classification Search
CPC .. G01N 33/24; G01N 2203/0256; G01N 3/10; G01N 3/08; G01N 2203/0254; G01N 13/04; G01N 15/0826; G01N 2203/0232
See application file for complete search history.

(56) References Cited

U.S. PATENT DOCUMENTS

| | | | | |
|---|---|---|---|---|
| 3,616,685 A | * | 11/1971 | Strom ...................... | G01N 3/02 73/84 |
| 4,825,700 A | * | 5/1989 | Vardoulakis ............. | G01N 3/08 73/749 |

(Continued)

*Primary Examiner* — David A Rogers
(74) *Attorney, Agent, or Firm* — Wayne & Ken, LLC; Tony Hom

(57) ABSTRACT

Disclosed is a simulation device for interaction between deep reservoir rock and fluid in a basin and a use method thereof. The simulation device for interaction between deep reservoir rock and fluid in basin includes an automatic control unit, a heating unit, a pressurizing unit, an analysis metering unit, and a peripheral auxiliary unit. An output end of the automatic control unit is electrically connected to input ends of the heating unit, the pressurizing unit, and the peripheral auxiliary unit in a one-way direction, respectively. An output end of the analysis metering unit is electrically connected to an input end of the automatic control unit in a one-way direction. Combining the automatic control unit, the heating unit, the pressurizing unit, the analysis metering unit, and the peripheral auxiliary unit, the present disclosure solves problems of unreasonable evaluation on the interaction between the deep reservoir rock and fluid in a basin.

10 Claims, 2 Drawing Sheets

(56) References Cited

U.S. PATENT DOCUMENTS

| | | | | |
|---|---|---|---|---|
| 5,159,828 A * | 11/1992 | Steiger | E21B 49/006 | 73/38 |
| 5,226,310 A * | 7/1993 | Steiger | E21B 49/006 | 73/38 |
| 5,275,063 A * | 1/1994 | Steiger | G01N 33/241 | 73/865.6 |
| 5,285,692 A * | 2/1994 | Steiger | E21B 49/005 | 73/866 |
| 5,606,133 A * | 2/1997 | Hines | B29C 43/04 | 73/818 |
| 5,698,789 A * | 12/1997 | Lainio | G01N 3/08 | 73/824 |
| 5,739,436 A * | 4/1998 | Trautwein | G01N 3/24 | 73/841 |
| 6,026,692 A * | 2/2000 | Brovold | B29C 43/04 | 73/818 |
| 6,729,189 B2 * | 5/2004 | Paakkinen | G01N 3/02 | 73/813 |
| 6,971,260 B2 * | 12/2005 | Potter | G01N 3/10 | 73/152.05 |
| 7,143,653 B2 * | 12/2006 | Abdel-Hadi | G01N 3/10 | 73/819 |
| 7,549,315 B2 * | 6/2009 | Bulled | G01N 3/10 | 73/11.01 |
| 8,234,912 B2 * | 8/2012 | Suarez-Rivera | G01N 3/46 | 73/78 |
| 8,375,802 B2 * | 2/2013 | Khoury | G01N 33/24 | 73/784 |
| 8,438,914 B2 * | 5/2013 | Martiska | G01N 3/08 | 73/788 |
| 8,561,474 B2 * | 10/2013 | Secq | E21B 21/08 | 73/825 |
| 8,770,038 B2 * | 7/2014 | Secq | E21B 21/08 | 73/783 |
| 8,800,353 B2 * | 8/2014 | Ng | G01N 33/24 | 73/73 |
| 9,316,572 B2 * | 4/2016 | Benet | G01N 3/08 | |
| 9,546,940 B2 * | 1/2017 | Gupta | G01N 33/24 | |
| 9,921,202 B2 * | 3/2018 | Huang | G01B 21/32 | |
| 10,145,775 B2 * | 12/2018 | Savari | G01N 7/00 | |
| 10,190,413 B2 * | 1/2019 | Smith | E21B 49/08 | |
| 10,324,227 B2 * | 6/2019 | Yang | G01N 7/00 | |
| 10,365,193 B2 * | 7/2019 | Feng | G01N 3/12 | |
| 10,472,788 B2 * | 11/2019 | Wang | E02D 3/10 | |
| 2004/0244497 A1 * | 12/2004 | Abdel-Hadi | G01N 3/10 | 73/819 |
| 2005/0150273 A1 * | 7/2005 | Potter | G01N 3/10 | 73/38 |
| 2008/0257030 A1 * | 10/2008 | Slavin | G01N 15/08 | 73/152.11 |
| 2011/0132099 A1 * | 6/2011 | Secq | E21B 21/08 | 73/821 |
| 2011/0214506 A1 * | 9/2011 | Khoury | G01N 33/24 | 73/784 |
| 2013/0002258 A1 * | 1/2013 | Ligneul | E21B 47/06 | 324/376 |
| 2013/0054157 A1 * | 2/2013 | Lasseux | G01N 15/0826 | 702/47 |
| 2013/0104629 A1 * | 5/2013 | Oh | G01N 15/0806 | 73/38 |

\* cited by examiner

SIMULATION DEVICE FOR INTERACTION BETWEEN DEEP RESERVOIR ROCK AND FLUID IN BASIN AND METHOD FOR USING SAME

CROSS-REFERENCE TO RELATED APPLICATIONS

This application claims to Chinese Application No. 201711347121.3 with a filing date of Dec. 15, 2017. The content of the aforementioned applications, including any intervening amendments thereto, are incorporated herein by reference.

TECHNICAL FIELD

The present disclosure relates to the technical field of mechanism of oil and gas accumulation and reservoir evaluation, and more specifically, to a simulation device for interaction between deep reservoir rock and fluid in a basin.

BACKGROUND

Interaction between reservoir rock and fluid is a quite complex geochemical process, subjected to many factors such as minerals, formation water, and physical and chemical conditions in a reservoir rock environment. The most important thing is the interaction between minerals and pore fluids. Fluid flow is a key factor affecting diagenesis. Distribution of diagenetic minerals in sandstones is related to particle size and effective porosity during deposition. The above parameters in turn are related to permeability and fluid flow. Diagenesis such as cementation and metasomatism of the reservoir rock is one function of a relationship between a solid phase and a pore fluid. This process is quite complex, and a chemical mechanism thereof is more complex. Generally, deep in a basin, a depth is more than 6000 m, and a confining pressure and a lithostatic pressure at least should be more than 150 MPa. Under conditions of high temperature (a geological temperature of greater than 150° C.) and high pressure (greater than 150 MPa) in a deep portion, physical and chemical properties (phase state, surface tension, viscosity, pH value and so on) of a reservoir fluid and an oil-gas-water multi-phase fluid change a lot. Finally, a process and a mechanism of the complex interaction between the fluid condition changes and rocks become more complicated.

Currently, simulation experiment technologies are used for evaluation of the process and the mechanism of the interaction between deep reservoir rock and fluid in a basin. Since researchers are unable to directly observe and directly measure the process of the interaction between deep reservoir rock and fluid in a basin, through the use of the simulation experiment technologies, researchers simulate the interaction between deep reservoir rock and fluid under conditions of certain temperature, lithostatic pressure, confining pressure, fluid pressure, geological time and so on. By measuring changes of various parameters of the rock and the fluid before and after the simulation experiment, the process and the mechanism of the interaction between deep reservoir rock and fluid in the basin are evaluated.

However, due to the fact that the fluid pressure, the lithostatic pressure, and the confining pressure of the reservoir rock are not matched with actual geological conditions, the evaluation on the interaction between the deep reservoir rock and fluid in a basin is unreasonable, and accuracy and preciseness of parameters after the interaction between rock and fluid are reduced. Therefore, we propose a simulation device for interaction between deep reservoir rock and fluid in a basin.

SUMMARY

The present disclosure is to provide a simulation device for interaction between deep reservoir rock and fluid in a basin, which has advantages of realizing a fluid pressure, a lithostatic pressure, and a confining pressure matched with actual geological conditions, and improving accuracy and preciseness of evaluation parameters of interaction between rock and fluid, and solves problems of unreasonable evaluation on the interaction between the deep reservoir rock and fluid in a basin, and reduced accuracy and preciseness of parameters after the interaction between the rock and fluid due to the fact that a fluid pressure, a lithostatic pressure, and a confining pressure of the reservoir rock are not matched with actual geological conditions.

In order to achieve the above object, the present disclosure provides a following technical solution: a simulation device for interaction between deep reservoir rock and fluid in a basin includes an automatic control unit, a heating unit, a pressurizing unit, an analysis metering unit, and a peripheral auxiliary unit. An output end of the automatic control unit is electrically connected to input ends of the heating unit, the pressurizing unit, and the peripheral auxiliary unit in a one-way direction, respectively, and an output end of the analysis metering unit is electrically connected to an input end of the automatic control unit in a one-way direction.

The heating unit includes a stand and a box type heater, each of two sides of the stand is fixedly mounted with a heating tube, a temperature-control thermocouple, a temperature-measurement thermocouple, and a power supply. At a back of the box type heater is fixedly mounted with a motor and a fan. A right side of the box type heater is connected to a control panel through a conducting line. The heating tube, the temperature-control thermocouple, the temperature-measurement thermocouple, and the power supply are connected to a heating button and a temperature controller head T on a surface of the control panel through a conducting line. On a top of the box type heater is fixedly mounted with an upper oil cylinder. A lithostatic compression rod is provided in a bottom of the upper oil cylinder. In a bottom of the box type heater is fixedly mounted with a lower oil cylinder. A lithostatic push rod is provided on a top of the lower oil cylinder. An upper condenser jacket is provided on a surface of the lithostatic compression rod. A lower condenser jacket is provided on a surface of the lithostatic push rod. A surface of the upper condenser jacket communicates with a water outlet silicone tube and a water inlet silicone tube. A surface of the lower condenser jacket communicates with the water outlet silicone tube and the water inlet silicone tube. Ends of the water outlet silicone tube and the water inlet silicone tube away from the box type heater communicate with a circulating water condenser, respectively.

The pressurizing unit includes a hydraulic unit oil pump and a micro-regulating back-pressure system. The hydraulic unit oil pump communicates with the upper oil cylinder through an inlet hydraulic oil pipe. The hydraulic unit oil pump communicates with the lower oil cylinder through an outlet hydraulic oil pipe. An upper oil cylinder inner piston is fixedly connected with a top of the lithostatic compression rod and is located inside the upper oil cylinder. A lower oil cylinder inner piston is fixedly connected to a bottom of the lithostatic push rod and is located inside the lower oil cylinder. In the box type heater is provided with a sample chamber. A sample is provided inside the sample chamber. Metal filters located inside the sample chamber are movably connected with two ends of the sample. A high-temperature high-pressure kettle is fixedly mounted inside the box type heater. The sample chamber is movably connected with inside of the high-temperature high-pressure kettle. Two ends of the sample chamber are respectively provided with a sealing element, an upper pressing jacket, and a lower pressing jacket. The lithostatic compression rod contacts with the upper pressing jacket. In a bottom of the high-temperature high-pressure kettle is provided with a lower end cover. A top of the lithostatic push rod penetrates through the lower end cover and contacts with the lower pressing jacket. An outlet conduit of the high-temperature high-pressure kettle passes through the upper pressing jacket and communicates with an upper right-angle elbow pipe. An inlet conduit of the high-temperature high-pressure kettle passes through the lower pressing jacket and communicates with a lower right-angle elbow pipe.

Preferably, an end of the upper right-angle elbow pipe away from the high-temperature high-pressure kettle communicates with a high-pressure three-way valve. A first exit end of the high-pressure three-way valve is fixedly connected with a first pressure sensor, and a second exit end of the high-pressure three-way valve is fixedly connected with an upper pneumatic valve. A bottom of the upper pneumatic valve is connected to an electromagnetic valve and an air compressor.

Preferably, the upper pneumatic valve is connected to, from left to right, a pressure controller, a gas-liquid separator, a gas collecting meter, a trace quantitative gas collector, a gas transferring device, a carrier gas, a heavy oil trap, and a filtering trap, and a bottom of the gas-liquid separator is connected to a cold trap.

Preferably, the filtering trap is connected to a pressure gauge head through a vacuum manifold. A terminal end of the pressure gauge head is connected to a sample introduction port of a gas chromatograph. The pressure gauge head is connected to a mechanical pump through a vacuum manifold. A terminal end of the mechanical pump is connected to a high-vacuum six-way valve.

Preferably, an inlet conduit of the high-temperature high-pressure kettle is connected to a lower pneumatic valve. A bottom of the lower pneumatic valve is connected to an electromagnetic valve. The air compressor is fixedly connected to a bottom of the lower pneumatic valve.

Preferably, the lower pneumatic valve is connected to a pressure-reducing valve through a vacuum manifold. The pressure-reducing valve is connected to a nitrogen cylinder through a vacuum manifold.

Preferably, the pressure-reducing valve is connected to a second pressure sensor through a vacuum manifold. The pressure-reducing valve is connected to a bottom portion of the pressure controller through a vacuum manifold. The second pressure sensor is connected to the control panel through a conducting line.

Preferably, the lower pneumatic valve is connected to a gas quantitative pipe through a vacuum manifold. The gas quantitative pipe is connected to a high-pressure intermediate container through a vacuum manifold.

Preferably, the gas quantitative pipe is connected successively to a third pressure sensor, a pressure-reducing valve, and a gas source through a vacuum manifold. The third pressure sensor is connected to the control panel through a conducting line.

Preferably, a bottom of the high-pressure intermediate container is fixedly connected to a high-pressure electric pump. The high-pressure electric pump is fixedly connected with a right side of the air compressor.

Compared with the prior art, the present disclosure has following beneficial effects:

1. the present disclosure provides with the automatic control unit, the heating unit, the pressurizing unit, the analysis metering unit, and the peripheral auxiliary unit, the automatic control unit includes a computer and proprietary software, the gauge head on the control panel for controlling the temperature, time, automatic gas dosing, and various pressures (including the confining pressure, the lithostatic pressure, and the fluid pressure), the pneumatic valve, the electromagnetic valve, and the power supply; the heating unit includes the box type heater, the heating tube, and the thermocouples, the fan with the motor and the power supply; the pressurizing unit includes the hydraulic unit oil pump, the inlet hydraulic oil pipe and the outlet hydraulic oil pipe, and the micro-regulating back-pressure system; the analysis metering unit includes the collecting meter for gas and liquid, and the analysis instrument for gas, liquid, and solid rock; the peripheral auxiliary unit includes the mechanical pump and the vacuum system, the air compressor, the high-pressure electric pump, and the intermediate container. Upon application of a sealing pressure, a confining pressure, and a lithostatic pressure to a cylindrical rock sample inside the high-temperature high-pressure kettle, a fluid pressure is generated and the fluid is heated, such that the rock and the fluid interact sufficiently under a condition of a high temperature and a high pressure, thus the interaction between deep reservoir rock and fluid in a basin is stimulated. By virtue of cooperation of the automatic control unit, the heating unit, the pressurizing unit, the analysis metering unit, and the peripheral auxiliary unit, it solves the problems of unreasonable evaluation on the interaction between the deep reservoir rock and fluid in a basin, and reduced accuracy and preciseness of parameters after the interaction between the rock and fluid due to the fact that the fluid pressure, the lithostatic pressure, and the confining pressure of the reservoir rock are not matched with actual geological conditions.

2. The present disclosure provides with the automatic control unit, the heating unit, the pressurizing unit, the analysis metering unit, and the peripheral auxiliary unit; the automatic control unit performs automatic control over the temperature, the pressure, and various other parameters through the computer and software, so as to reach design values in the experiment; design values of the temperature, the lithostatic pressure, and the confining pressure are achieved by the heating unit and the pressurizing unit; parameters of the rock and the fluid before and after the experiment are measured by the analysis metering unit; the peripheral auxiliary unit provides a vacuum system, a fluid pressure and so on. The automatic control unit controls the heating unit, the pressurizing unit, the analysis metering unit, and the peripheral auxiliary unit.

Figure 1:
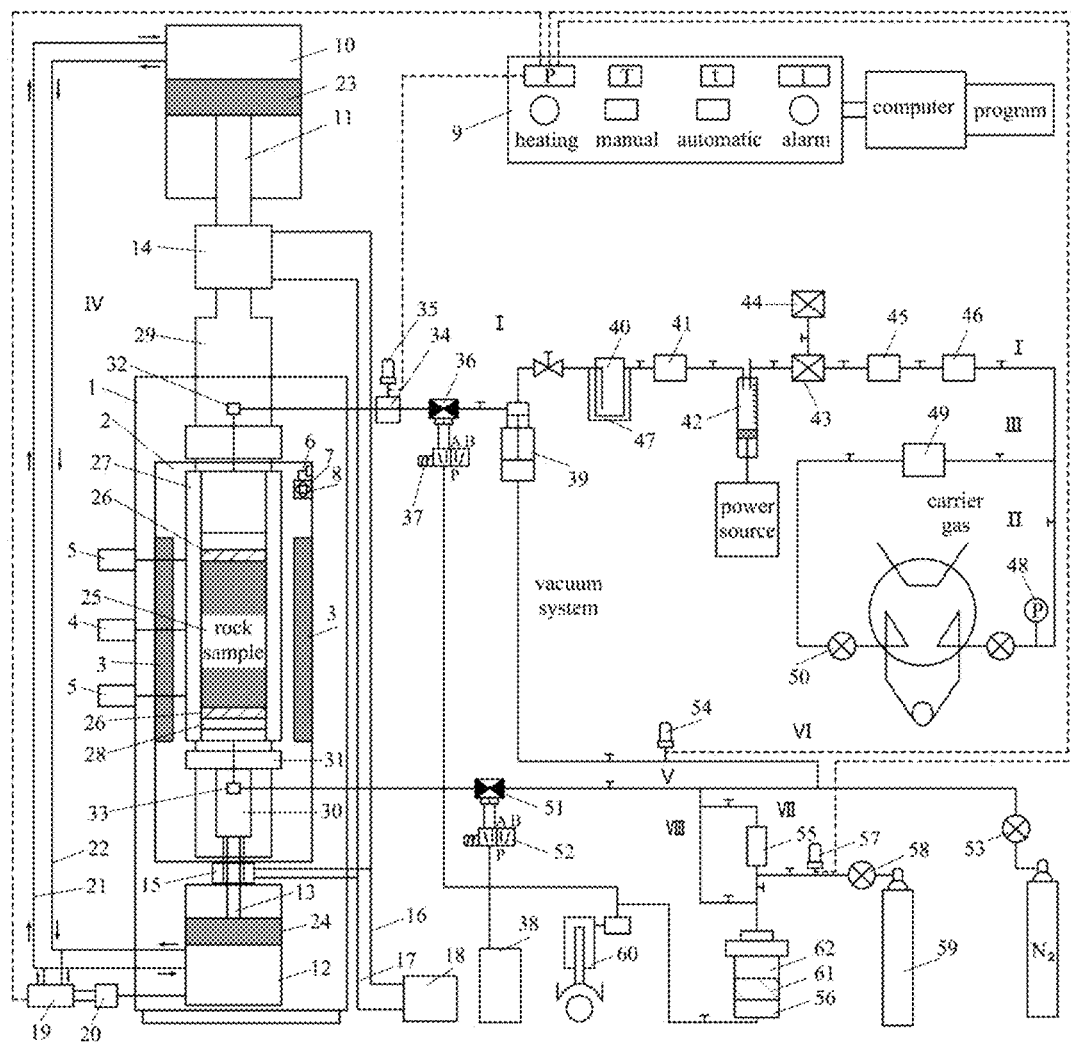
FIG. 1 is a structural schematic diagram according to the present disclosure.

In the drawings: 1 stand, 2 boxtype heater, 3 heating tube, 4 temperature-control thermocouple, 5 temperature-measurement thermocouple, 6 power supply, 7 motor, 8 fan, 9 control panel, 10 upper oil cylinder, 11 lithostatic compression rod, 12 lower oil cylinder, 13 lithostatic push rod, 14 upper condenser jacket, 15 lower condenser jacket, 16 water outlet silicone tube, 17 water inlet silicone tube, 18 circulating water condenser, 19 hydraulic unit oil pump, 20 micro-regulating back-pressure system, 21 inlet hydraulic oil pipe, 22 outlet hydraulic oil pipe, 23 upper oil cylinder inner piston, 24 lower oil cylinder inner piston, 25 sample chamber, 26 metal filter, 27 high-temperature high-pressure kettle, 28 sealing element, 29 upper pressing jacket, 30 lower pressing jacket, 31 lower end cover, 32 upper right-angle elbow pipe, 33 lower right-angle elbow pipe, 34 high-pressure three-way valve, 35 first pressure sensor, 36 upper pneumatic valve, 37 electromagnetic valve, 38 air compressor, 39 pressure controller, 40 gas-liquid separator, 41 gas collecting meter, 42 trace quantitative gas collector, 43 gas transferring device, 44 carrier gas, 45 heavy oil trap, 46 filtering trap, 47 connection cold trap, 48 pressure gauge head, 49 mechanical pump, 50 high-vacuum six-way valve, 51 lower pneumatic valve, 52 connection electromagnetic valve, 53 pressure-reducing valve, 54 second pressure sensor, 55 gas quantitative pipe, 56 high-pressure intermediate container, 57 third pressure sensor, 58 pressure-reducing valve, 59 gas source, 60 high-pressure electric pump.

DETAILED DESCRIPTION

Below technical solutions of embodiments of the present disclosure will be described clearly and completely in conjunction with accompanying drawings in the embodiments of the present disclosure. Apparently, some but not all of embodiments of the present disclosure are described. On the basis of the embodiments in the present disclosure, all of other embodiments obtained by a person ordinarily skilled in the art without inventive effort fall within the scope of protection of the present disclosure.

Figure 2:
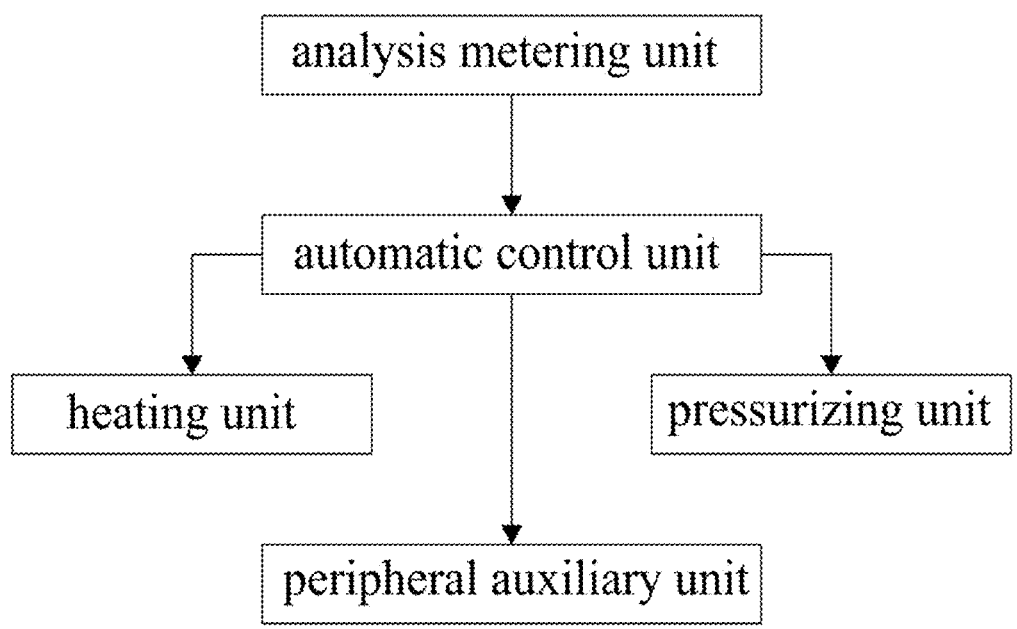
FIG. 2 is a system principle diagram according to the present disclosure.

Referring to FIGS. 1-2, a simulation device for interaction between deep reservoir rock and fluid in a basin includes an automatic control unit, a heating unit, a pressurizing unit, an analysis metering unit, and a peripheral auxiliary unit. An output end of the automatic control unit is electrically connected to input ends of the heating unit, the pressurizing unit, and the peripheral auxiliary unit in a one-way direction, respectively. An output end of the analysis metering unit is electrically connected to an input end of the automatic control unit in a one-way direction.

The heating unit includes a stand 1 and a box type heater 2. Each of two sides of the stand 1 is fixedly mounted with a heating tube 3, a temperature-control thermocouple 4, a temperature-measurement thermocouple 5, and a power supply 6. At a back of the box type heater 2 is fixedly mounted with a motor 7 and a fan 8. A right side of the box type heater 2 is connected to a control panel 9 through a conducting line. The heating tube 3, the temperature-control thermocouple 4, the temperature-measurement thermocouple 5, and the power supply 6 are connected to a heating button and a temperature controller head T on a surface of the control panel 9 through a conducting line. On a top of the box type heater 2 is fixedly mounted with an upper oil cylinder 10. A lithostatic compression rod 11 is provided in a bottom of the upper oil cylinder 10. In a bottom of the box type heater 2 is fixedly mounted with a lower oil cylinder 12. A lithostatic push rod 13 is provided on a top of the lower oil cylinder 12. An upper condenser jacket 14 is provided on a surface of the lithostatic compression rod 11. A lower condenser jacket 15 is provided on a surface of the lithostatic push rod 13. A surface of the upper condenser jacket 14 communicates with a water outlet silicone tube 16 and a water inlet silicone tube 17. A surface of the lower condenser jacket 15 communicates with the water outlet silicone tube 16 and the water inlet silicone tube 17. Ends of the water outlet silicone tube 16 and the water inlet silicone tube 17 away from the box type heater 2 communicate with a circulating water condenser 18, respectively.

The pressurizing unit includes a hydraulic unit oil pump 19 and a micro-regulating back-pressure system 20. The hydraulic unit oil pump 19 communicates with the upper oil cylinder 10 through an inlet hydraulic oil pipe 21. The hydraulic unit oil pump 19 communicates with the lower oil cylinder 12 through an outlet hydraulic oil pipe. An upper oil cylinder inner piston 23 is fixedly connected to a top of the lithostatic compression rod 11 and is located inside the upper oil cylinder 10. A lower oil cylinder inner piston 24 is fixedly connected to a bottom of the lithostatic push rod 13 and is located inside the lower oil cylinder 12. In the box type heater 2 is provided with a sample chamber 25. A sample is provided inside the sample chamber 25. Metal filters 26 located inside the sample chamber 25 are movably connected with two ends of the sample. A high-temperature high-pressure kettle 27 is fixedly mounted inside the box type heater 2. The sample chamber 25 is movably connected with the inside of the high-temperature high-pressure kettle 27. Two ends of the sample chamber 25 are respectively provided with a sealing element 28, an upper pressing jacket 29, and a lower pressing jacket 30. The lithostatic compression rod 11 contacts with the upper pressing jacket 29. In a bottom of the high-temperature high-pressure kettle 27 is provided with a lower end cover 31. A top of the lithostatic push rod 13 penetrates through the lower end cover 31 and contacts with the lower pressing jacket 30. An outlet conduit of the high-temperature high-pressure kettle 27 passes through the upper pressing jacket 29 and communicates with an upper right-angle elbow pipe 32. An inlet conduit of the high-temperature high-pressure kettle 27 passes through the lower pressing jacket 30 and communicates with a lower right-angle elbow pipe 33. An end of the upper right-angle elbow pipe 32 away from the high-temperature high-pressure kettle 27 communicates with a high-pressure three-way valve 34. A first exit end of the high-pressure three-way valve 34 is fixedly connected with a first pressure sensor 35, and a second exit end of the high-pressure three-way valve 34 is fixedly connected with an upper pneumatic valve 36. A bottom of the upper pneumatic valve 36 is connected to an electromagnetic valve 37 and an air compressor 38. The upper pneumatic valve 36 is connected to, from left to right, a pressure controller 39, a gas-liquid separator 40, a gas collecting meter 41, a trace quantitative gas collector 42, a gas transferring device 43, a carrier gas 44, a heavy oil trap 45, and a filtering trap 46. A bottom of the gas-liquid separator 40 is connected to a cold trap 47. The filtering trap 46 is connected to a pressure gauge head 48 through a vacuum manifold. A terminal end of the pressure gauge head 48 is connected to a sample introduction port of a gas chromatograph. The pressure gauge head 48 is connected to a mechanical pump 49 through a vacuum manifold. A terminal end of the mechanical pump 49 is connected to a high-vacuum six-way valve 50. An inlet conduit of the high-temperature high-pressure kettle 27 is connected to a lower pneumatic valve 51. A bottom of the lower pneumatic valve 51 is connected to a connection electromagnetic valve 52. The air compressor 38 is fixedly connected to a bottom of the lower pneumatic valve 51. The lower pneumatic valve 51 is connected to a pressure-reducing valve 58 through a vacuum manifold. The pressure-reducing valve 58 is connected to a nitrogen cylinder through a vacuum manifold. The pressure-reducing valve 58 is connected to a second pressure sensor 54 through a vacuum manifold. The pressure-reducing valve 58 is connected to a bottom of the pressure controller 39 through a vacuum manifold. The second pressure sensor 54 is connected to the control panel 9 through a conducting line. The lower pneumatic valve 51 is connected to a gas quantitative pipe 55 through a vacuum manifold. The gas quantitative pipe 55 is connected to a high-pressure intermediate container 56 through a vacuum manifold. The gas quantitative pipe 55 is connected successively to a third pressure sensor 57, a pressure-reducing valve 58, and a gas source 59 through a vacuum manifold. The third pressure sensor 57 is connected to the control panel 9 through a conducting line. A bottom of the high-pressure intermediate container 56 is fixedly connected to a high-pressure electric pump 60. The high-pressure electric pump 60 is fixedly connected with a right side of the air compressor 38. By providing the automatic control unit, the heating unit, the pressurizing unit, the analysis metering unit, and the peripheral auxiliary unit, the automatic control unit performs automatic control over the temperature, the pressure, and various other parameters through the computer and software, so as to reach design values in the experiment. Design values of the temperature, the lithostatic pressure, and the confining pressure are achieved by the heating unit and the pressurizing unit. Parameters of the rock and the fluid before and after the experiment are measured by the analysis metering unit. The peripheral auxiliary unit provides a vacuum system, a fluid pressure and so on. The automatic control unit controls the heating unit, the pressurizing unit, the analysis metering unit, and the peripheral auxiliary unit. By providing the automatic control unit, the heating unit, the pressurizing unit, the analysis metering unit, and the peripheral auxiliary unit, the automatic control unit includes a computer and proprietary software, the gauge head on the control panel 9 for controlling the temperature, time, automatic gas dosing, and various pressures including the confining pressure, the lithostatic pressure, and the fluid pressure, the pneumatic valves 36 and 51, the electromagnetic valve 37, and the power supply 6; the heating unit includes the box type heater 2, the heating tube 3, the temperature-control thermocouple 4 and the temperature-measurement thermocouple 5, the fan 8 with a motor 7 and the power supply 6; the pressurizing unit includes the hydraulic unit oil pump 19, the inlet hydraulic oil pipe 21, the outlet hydraulic oil pipe 22, and the micro-regulating back-pressure system 20; the analysis metering unit includes the collecting meter for gas and liquid and the analysis instrument for gas, liquid, and solid rock; the peripheral auxiliary unit includes the mechanical pump 49 and the vacuum system, the air compressor 38, the high-pressure electric pump 60, and the intermediate container. Upon application of a sealing pressure, a confining pressure, and a lithostatic pressure to a cylindrical rock sample inside the high-temperature high-pressure kettle 27, a fluid pressure is generated and the fluid is heated, such that the rock and the fluid interact sufficiently under a condition of a high temperature and a high pressure, thus the interaction between deep reservoir rock and fluid in a basin is stimulated. By virtue of cooperation of the automatic control unit, the heating unit, the pressurizing unit, the analysis metering unit, and the peripheral auxiliary unit, it solves the problems of unreasonable evaluation on the interaction between the deep reservoir rock and fluid in a basin, and reduced accuracy and preciseness of parameters after the interaction between the rock and fluid due to the fact that the fluid pressure, the lithostatic pressure, and the confining pressure of the reservoir rock are not matched with actual geological conditions.

In use, before the simulation experiment, the design values of the temperature, the fluid pressure, the lithostatic pressure, and the confining pressure of the reservoir rock are obtained from precise calculation of a geological model of a petroliferous basin under research, and during the simulation experiment, a sedimentation process and an uplifting process of the interaction between the deep reservoir rock and the fluid are realized.

The sedimentation process of the interaction between the deep reservoir rock and the fluid is a heating and pressurizing process, the box type heater 2, the heating tube 3, the thermocouples, and the fan 8 with the motor 7 are utilized to form hot wind circulating up and down with similar temperature, to heat the rock and the fluid inside the sample chamber 25 of the high-temperature high-pressure kettle 27; a continuous variable mechanical pressure is produced by a hydraulic unit to simulate the lithostatic pressure, and by increasing a volume of the hydraulic oil inside the upper oil cylinder 10, the lithostatic pressure applied on an upper surface of the rock sample is increased; by increasing a pressure of the high-pressure electric pump 60, the fluid pressure born by the rock sample inside the sample chamber 25 of the high-temperature high-pressure kettle 27 is increased, thus the sedimentation process of the interaction between the deep reservoir rock and the fluid is completely simulated.

The uplifting process of the interaction between the deep reservoir rock and the fluid is a cooling and de-pressurizing process, the heating tube 3 inside the box type heater 2 stops heating, the fan 8 with the motor 7 blows hot wind out of the heater, so as to cool the rock and the fluid inside the sample chamber 25 of the high-temperature high-pressure kettle 27; a continuous variable mechanical pressure is produced by the hydraulic unit to simulate the lithostatic pressure, and by decreasing the volume of the hydraulic oil inside the upper oil cylinder 10, the lithostatic pressure applied on the upper surface of the rock sample is decreased; by decreasing the pressure of the high-pressure electric pump 60, the fluid pressure born by the rock sample inside the sample chamber 25 of the high-temperature high-pressure kettle 27 is decreased, thus the uplifting process of the interaction between the deep reservoir rock and the fluid is completely simulated.

Through the precise control of software and hardware, the parameter values of the temperature and various pressures are equivalent to the design values, and approximate the actual geological temperature-pressure condition, thus, the accuracy and preciseness of parameters after the interaction between the rock and fluid are improved, and accordingly the process and the mechanism of the interaction between the deep reservoir rock and fluid in a basin is precisely evaluated.

To sum up, by virtue of cooperation of the automatic control unit, the heating unit, the pressurizing unit, the analysis metering unit, and the peripheral auxiliary unit, the simulation device for interaction between deep reservoir rock and fluid in a basin solves the problems of unreasonable evaluation on the interaction between the deep reservoir rock and fluid in a basin, and reduced accuracy and preciseness of parameters after the interaction between the rock and fluid due to the fact that the fluid pressure, the lithostatic pressure, and the confining pressure of the reservoir rock are not matched with the actual geological conditions.

Although the embodiments of the present disclosure have been shown and described, for a person ordinarily skilled in the art, many changes, alterations, substitutions, and modifications may be made to these embodiments, without departing from the principle and spirit of the present disclosure. The scope of the present disclosure is defined by the attached claims and equivalents thereof.

What is claimed is:

1. A simulation device for interaction between deep reservoir rock and fluid in a basin, comprising an automatic control unit, a heating unit, a pressurizing unit, an analysis metering unit, and a peripheral auxiliary unit; wherein an output end of the automatic control unit is electrically connected to input ends of the heating unit, the pressurizing unit, and the peripheral auxiliary unit in a unidirectional manner; an output end of the analysis metering unit is electrically connected to an input end of the automatic control unit in a one-way direction;

the heating unit comprises a stand (1) and a box type heater (2); each of two sides of the stand (1) is fixedly mounted with a heating tube (3), a temperature-control thermocouple (4), a temperature-measurement thermocouple (5), and a power supply (6); at a back of the box type heater (2) is fixedly mounted with a motor (7) and a fan (8); a right side of the box type heater (2) is connected to a control panel (9) through a conducting line; the heating tube (3), the temperature-control thermocouple (4), the temperature-measurement thermocouple (5), and the power supply (6) are connected to a heating button and a temperature controller head T on a surface of the control panel (9) through a conducting line; on a top of the box type heater (2) is fixedly mounted with an upper oil cylinder (10); a lithostatic compression rod (11) is provided in a bottom of the upper oil cylinder (10); in a bottom of the box type heater (2) is fixedly mounted with a lower oil cylinder (12); a lithostatic push rod (13) is provided on a top of the lower oil cylinder (12); an upper condenser jacket (14) is provided on a surface of the lithostatic compression rod (11); a lower condenser jacket (15) is provided on a surface of the lithostatic push rod (13); a surface of the upper condenser jacket (14) is communicated with a water outlet silicone tube (16); a surface of the lower condenser jacket (15) is communicated with a water inlet silicone tube (17); ends of the water outlet silicone tube (16) and the water inlet silicone tube (17) away from the box type heater (2) are communicated with a circulating water condenser (18), respectively;

the pressurizing unit comprises a hydraulic unit oil pump (19) and a micro-regulating back-pressure system (20); the hydraulic unit oil pump (19) is communicated with the upper oil cylinder (10) through an inlet hydraulic oil pipe (21); the hydraulic unit oil pump (19) is communicated with the lower oil cylinder (12) through an outlet hydraulic oil pipe (22); an upper oil cylinder inner piston (23) is fixedly connected with a top of the lithostatic compression rod (11) and is located inside the upper oil cylinder (10); a lower oil cylinder inner piston (24) is fixedly connected with a bottom of the lithostatic push rod (13) and is located inside the lower oil cylinder (12); in the box type heater (2) is provided with a sample chamber (25); a sample is provided inside the sample chamber (25); metal filters (26) located inside the sample chamber (25) are movably connected with two ends of the sample; inside the box type heater (2) is fixedly mounted with a high-temperature high-pressure kettle (27); the sample chamber (25) is movably connected with the inside of the high-temperature high-pressure kettle (27); each of two ends of the sample chamber (25) is respectively provided with a sealing element (28), an upper pressing jacket (29), and a lower pressing jacket (30); the lithostatic compression rod (11) is in contact with the upper pressing jacket (29); in a bottom of the high-temperature high-pressure kettle (27) is provided with a lower end cover (31); a top of the lithostatic push rod (13) passes through the lower end cover (31) and is in contact with the lower pressing jacket (30); an outlet conduit of the high-temperature high-pressure kettle (27) passes through the upper pressing jacket (29) and is communicated with an upper right-angle elbow pipe (32); and an inlet conduit of the high-temperature high-pressure kettle (27) passes through the lower pressing jacket (30) and is communicated with a lower right-angle elbow pipe (33).

2. The simulation device for interaction between deep reservoir rock and fluid in a basin according to claim 1, wherein an end of the upper right-angle elbow pipe (32) away from the high-temperature high-pressure kettle (27) is communicated with a high-pressure three-way valve (34); a first exit end of the high-pressure three-way valve (34) is fixedly connected with a first pressure sensor (35); and a second exit end of the high-pressure three-way valve (34) is fixedly connected with an upper pneumatic valve (36); and a bottom of the upper pneumatic valve (36) is connected to an electromagnetic valve (37) and an air compressor (38).

3. The simulation device for interaction between deep reservoir rock and fluid in a basin according to claim 2, wherein the upper pneumatic valve (36) is connected to, from left to right, a pressure controller (39), a gas-liquid separator (40), a gas collecting meter (41), a trace quantitative gas collector (42), a gas transferring device (43), a carrier gas (44), a heavy oil trap (45), and a filtering trap (46); and a bottom of the gas-liquid separator (40) is connected to a cold trap (47).

4. The simulation device for interaction between deep reservoir rock and fluid in a basin according to claim 3, wherein the filtering trap (46) is connected to a pressure gauge head (48) through a vacuum manifold; a terminal end of the pressure gauge head (48) is connected to a sample introduction port of a gas chromatograph; the pressure gauge head (48) is connected to a mechanical pump (49) through a vacuum manifold; and a terminal end of the mechanical pump (49) is connected to a high-vacuum six-way valve (50).

5. The simulation device for interaction between deep reservoir rock and fluid in a basin according to claim 1, wherein an inlet conduit of the high-temperature high-pressure kettle (27) is connected to a lower pneumatic valve (51); a bottom of the lower pneumatic valve (51) is connected to a connection electromagnetic valve (52); and the air compressor (38) is fixedly connected to a bottom of the lower pneumatic valve (51).

6. The simulation device for interaction between deep reservoir rock and fluid in a basin according to claim 5, wherein the lower pneumatic valve (51) is connected to a pressure-reducing valve (58) through a vacuum manifold; and the pressure-reducing valve (58) is connected to a nitrogen cylinder through a vacuum manifold.

7. The simulation device for interaction between deep reservoir rock and fluid in a basin according to claim 6, wherein the pressure-reducing valve (58) is connected to a second pressure sensor (54) through a vacuum manifold; the pressure-reducing valve (58) is connected to a bottom of the pressure controller (39) through a vacuum manifold; and the second pressure sensor (54) is connected to the control panel (9) through a conducting line.

8. The simulation device for interaction between deep reservoir rock and fluid in a basin according to claim 5, wherein the lower pneumatic valve (51) is connected to a gas quantitative pipe (55) through a vacuum manifold; and the gas quantitative pipe (55) is connected to a high-pressure intermediate container (56) through a vacuum manifold.

9. The simulation device for interaction between deep reservoir rock and fluid in a basin according to claim 8, wherein the gas quantitative pipe (55) is connected successively to a third pressure sensor (57), the pressure-reducing valve (58), and a gas source (59) through a vacuum manifold; the third pressure sensor (57) is connected to the control panel (9) through a conducting line; a bottom of the high-pressure intermediate container (56) is fixedly connected to a high-pressure electric pump (60); and the high-pressure electric pump (60) is fixedly connected to a right side of the air compressor (38).

10. A method for using the simulation device for interaction between deep reservoir rock and fluid in a basin, comprising:
  obtaining design values of a temperature, a fluid pressure, a lithostatic pressure, and a confining pressure of reservoir rock from precise calculation of a geological model of a petroliferous basin under research before a simulation experiment when in use; and
  realizing a sedimentation process and an uplifting process of interaction between deep reservoir rock and fluid during the simulation experiment; wherein the sedimentation process of the interaction between deep reservoir rock and fluid is a heating and pressurizing process; the box type heater (2), the heating tube (3), thermocouples, and the fan (8) having the motor (7) are utilized to form hot wind circulating up and down with similar temperature to heat rock and fluid inside the sample chamber (25) of the high-temperature high-pressure kettle (27); a continuous variable mechanical pressure is produced by a hydraulic unit to simulate the lithostatic pressure, and the lithostatic pressure applied on an upper surface of the rock sample is increased by increasing a volume of the hydraulic oil inside the upper oil cylinder (10); the fluid pressure born by the rock sample inside the sample chamber (25) of the high-temperature high-pressure kettle (27) is increased by increasing a pressure of the high-pressure electric pump (60); and the sedimentation process of the interaction between the deep reservoir rock and the fluid is completely simulated;
  the uplifting process of the interaction between the deep reservoir rock and the fluid is a cooling and depressurizing process; the heating tube (3) inside the box type heater (2) stops heating, the fan (8) having the motor (7) blows hot wind out of the box type heater, so as to cool the rock and the fluid inside the sample chamber (25) of the high-temperature high-pressure kettle (27); a continuous variable mechanical pressure is produced by the hydraulic unit to simulate the lithostatic pressure; the lithostatic pressure applied on the upper surface of the rock sample is decreased by decreasing the volume of the hydraulic oil inside the upper oil cylinder (10); the fluid pressure born by the rock sample inside the sample chamber (25) of the high-temperature high-pressure kettle (27) is decreased by decreasing the pressure of the high-pressure electric pump (60); the uplifting process of the interaction between the deep reservoir rock and the fluid is completely simulated;
  parameter values of the temperature and various pressures are equivalent to the design values, and approximate actual geological temperature-pressure condition through precise control of software and hardware; accuracy and preciseness of parameters after the interaction between the rock and fluid are improved; and accordingly a process and a mechanism of the interaction between the deep reservoir rock and fluid in a basin is precisely evaluated.

\* \* \* \* \*